United States Patent [19]
Jindo et al.

[11] Patent Number: 4,674,333
[45] Date of Patent: Jun. 23, 1987

[54] MULTI-COLOR DISPLAYING ULTRASONIC MICROSCOPE

[75] Inventors: Takeo Jindo; Ryosuke Suganuma, both of Aich, Japan

[73] Assignee: Keisuke Honda, Aichi, Japan

[21] Appl. No.: 780,386

[22] Filed: Sep. 26, 1985

[51] Int. Cl.$^4$ .......................................... G01N 29/04
[52] U.S. Cl. .................................................. 73/606
[58] Field of Search ................................. 73/606, 596

[56] References Cited
U.S. PATENT DOCUMENTS 3,292,018  12/1966  Clynes ................................... 73/628
4,026,144  5/1977  Gericke et al. ......................... 73/596

Primary Examiner—Anthony V. Ciarlante
Attorney, Agent, or Firm—Burgess, Ryan & Wayne

[57] ABSTRACT

Ultrasonic waves are reflected on or passed through a sample by a focusing ultrasonic transmitting element and a focusing ultrasonic receiving element or a focusing ultrasonic transmitting-receiving element, and two signals are produced by operating the ultrasonic waves or by changing conditions and are displayed as one image on a color cathode ray tube by changing the color.

3 Claims, 2 Drawing Figures

# MULTI-COLOR DISPLAYING ULTRASONIC MICROSCOPE

BACKGROUND OF THE INVENTION

The present invention relates to a color multidisplaying ultrasonic microscope for displaying changes of ultrasonic waves reflected on or passing through a sample to be inspected.

Generally, in the ultrasonic microscope, an image is displayed in a cathode ray tube by modulating its brilliance. When two images detected by the ultrasonic wave reflected on or passing through a sample under different conditions are compared with each other, the two images are respectively displayed on the cathode ray tube in black-and-white and are visually compared. However, comparison between the two images in black-and-white is not easy. Also, when the above two images are displayed in the cathode ray tube in color, each of two images is displayed by many colors corresponding to levels of the ultrasonic waves reflected on or passing through a sample to be inspected. Therefore, comparison between the two color images is difficult as well as in the case of the black-and-white images. Moreover, it is difficult to correct the order of the color display corresponding to the levels of the ultrasonic wave from the sample.

SUMMARY OF THE INVENTION

It is, therefore, a primary object of the present invention to provide a multi-color displaying ultrasonic microscope in which comparison between two images of the ultrasonic wave is easy.

It is another object of the present invention to provide a multi-color displaying ultrasonic microscope in which the images are displayed in the color cathode ray tube device by a change between two colors and the comparison between the two images is easy.

It is still another object of the present invention to provide a multi-color displaying ultrasonic microscope in which one image obtained under a predetermined condition is modulated by one color, the other image obtained under the other condition is modulated by another color, the two images are displayed as one image and thus the comparison between two images is very easy.

It is still another object of the present invention to provide a multi-color displaying ultrasonic microscope in which data of a sample in the depth direction and data of the frequency dependency of a sample are easily obtained.

In order to accomplish the above and other objects, the present invention comprises means for transmitting ultrasonic waves from an ultrasonic transmitting element or ultrasonic transmitting-receiving element to a sample to be inspected, means for detecting in an ultrasonic receiving element or the ultrasonic transmitting-receiving element the ultrasonic waves changed on the surface or inside of the sample by being reflected on the surface of the sample or by passing through the inside of the sample during movement of the ultrasonic transmitting and receiving elements, means for moving the ultrasonic transmitting-receiving element or the sample in X-Y direction, means for producing two signals by calculating the detected ultrasonic waves or by changing conditions, and means for displaying the two signals in a cathode ray tube device as one color image having a two color change.

These and other objects, features and advantages of the invention will become more apparent from the following description taken in connection with the illustrated embodiment of the accompanying drawings.

DESCRIPTION OF THE PREFERRED EMBODIMENTS

Figure 1:
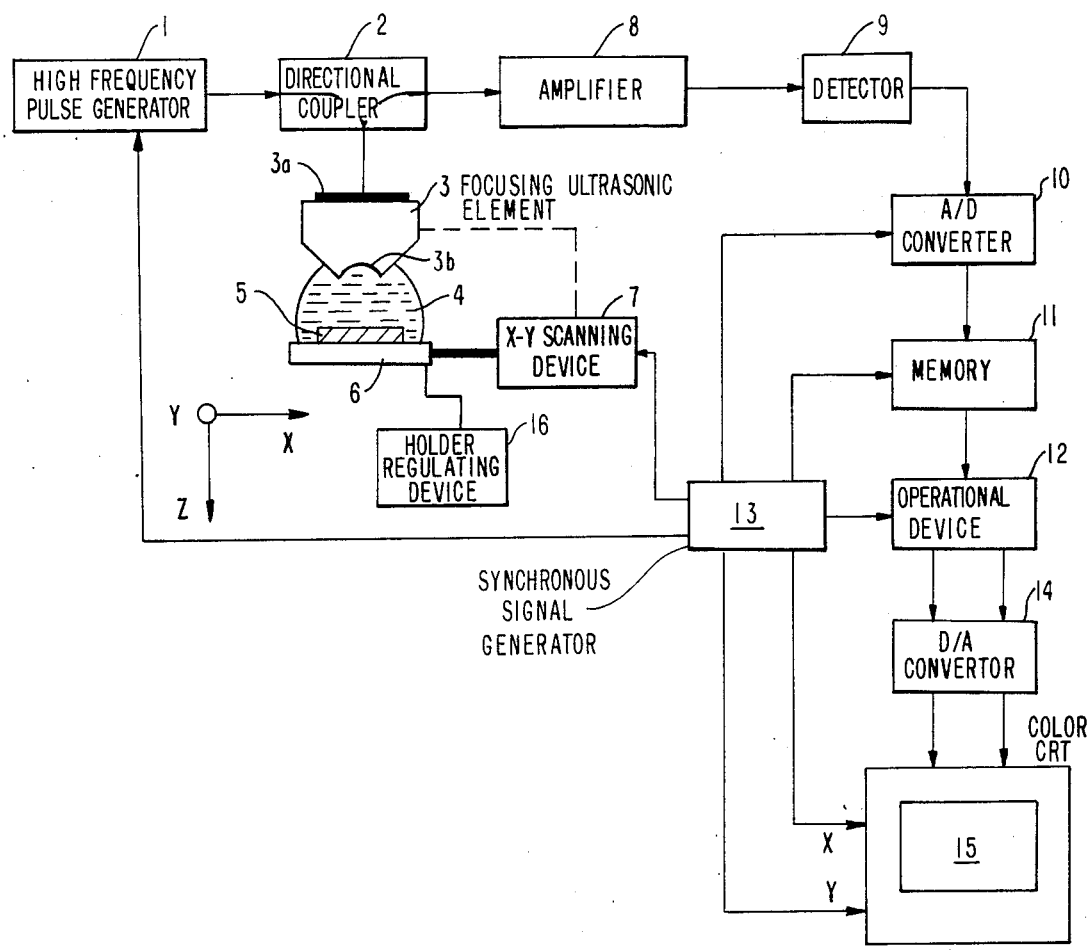
FIG. 1 illustrates a schematic block diagram of an embodiment of the present invention.

Referring to FIG. 1 of the drawings, the output terminal of a high frequency pulse generator 1 is connected to the transducer 3a of a focusing ultrasonic element 3 through a directional coupler 2. The lens portion 3b of the focusing ultrasonic element 3 is opposed to a sample in a liquid acoustic medium 4, and sample 5 is mounted on a sample holder 6. The sample holder 6 is provided with an X-Y scanning device 7 for moving the sample 5 in the X-Y direction and a holder regulating device 16 for regulating a gap between the sample 5 and the lens portion 3b of the focusing ultrasonic element 3. The focusing ultrasonic element 3 can be moved in the X-Y direction instead of the sample holder 6 as shown by a dotted line.

The output terminal of the directional coupler 2 is connected to an amplifier 8, the output terminal of which is connected to a detector 9. The output terminal of the detector 9 is connected to a memory device 11 though an A/D converter 10. The output terminal of the memory device 11 is connected to a color cathode ray tube 15 through an operation device 12 and a D/A converter 14. The output terminals of a synchronous signal generator 13 are respectively connected to the high frequency pulse generator 1, the X-Y scanning device 7, the A/D converter 10, the memory device 11, the operation device 12 and the color cathode ray tube 15.

The mode of operation of this embodiment will now be described. The high frequency pulse signals from the high frequency pulse generator 1, which are gated by the synchronous signals of the synchronous signal generator 13, are transmitted to the transducer 3a of the focusing ultrasonic element 3 through the directional coupler 2 and are converted thereat to ultrasonic waves. These ultrasonic waves irradiate the sample 5 mounted on the sample holder 6. The sample holder 6 is moved in the X-Y direction by the X-Y scanning device 7. The ultrasonic waves reflected by the sample 5 are converted to electric signals by the transducer 3a of the focusing ultrasonic element 3. The electric signals are amplified by the amplifier 8 and then are detected by the detector 9. The detected signals are converted to digital values in the A/D converter 10 by the converting signal from the synchronous signal generator 13 and the digital values are stored in the memory device 11. The digital values are operated on with other digital values by the operation device 12 as described hereinafter. The operated values are converted to analogue signals by three sections (not shown) in the D/A converter 14 respectively connected to the red, blue and green color electron guns in the color cathode ray tube 15. The analogue signals are applied to the color cathode ray tube 15 synchronously controlled by the synchronous signals from the synchronous generator 13 and a color image of the ultrasonic microscope is displayed on the cathode ray tube 15.

For example, the digital value [a] is applied from the operation device 12 to the first section of D/A converter 14 connected to the red electron gun and the reciprocal number [a'] of the digital value [a] is applied from the operation device 12 to the second section of D/A converter 14 connected to the green electron gun in the cathode ray tube 15. Two color images changed by red and green are displayed on the color cathode ray tube 15. Therefore, comparison between the color changed images is easier than with a black-and-white image, the brilliance of which is modulated.

Generally, in the ultrasonic microscope, data in the depth direction of the sample is required. When the sample holder 6 is so regulated by the holder regulating device 16 that the ultrasonic waves are focused on the surface of the sample 5 and the digital signals from the operation device 12 are applied to the first section of D/A converter 14 connected to the red electron gun, the color image [A] modulated by red is obtained. Similarly, when the sample holder 6 is so regulated by the holder regulating device 16 that the ultrasonic waves are focused in 100μ below the surface of the sample 5 and the digital signals from the operation device 12 are applied to the second section of D/A converter 14 connected to the green electron gun, the color image [B] modulated by green is obtained. When these color modulated images [A] and [B] are displayed on the color cathode ray tube 15, the color image [C] modulated by red and green is displayed and comparison between the two images is easily executed.

When the sample holder 6 is so regulated by the holder regulating device 16 that the ultrasonic waves are focused in 90μ below the surface of the sample 5, the digital value [d] is obtained. When the digital wave [d] is subtracted from the digital value [b] of the above color modulated image [B], the digital value [e] is obtained. This digital value [e] is applied to the third section of D/A cnverter 14 connected to the blue electron gun and the color image [E] modulated by blue is displayed with the above color image [B] modulated by green by the cathode ray tube 15. Therefore, this color image emphasized by the data in 90μ ~ 100μ below the surface of the sample 5 is obtained. The data in the predetermined depth below the surface of the sample 5 is easily obtained.

When the color modulated images [A] and [B] are obtained by changing the frequency of the output pulse from the high frequency pulse generator 1, the frequency dependency of the sample 5 is inspected by these color images according to the different frequencies.

Figure 2:
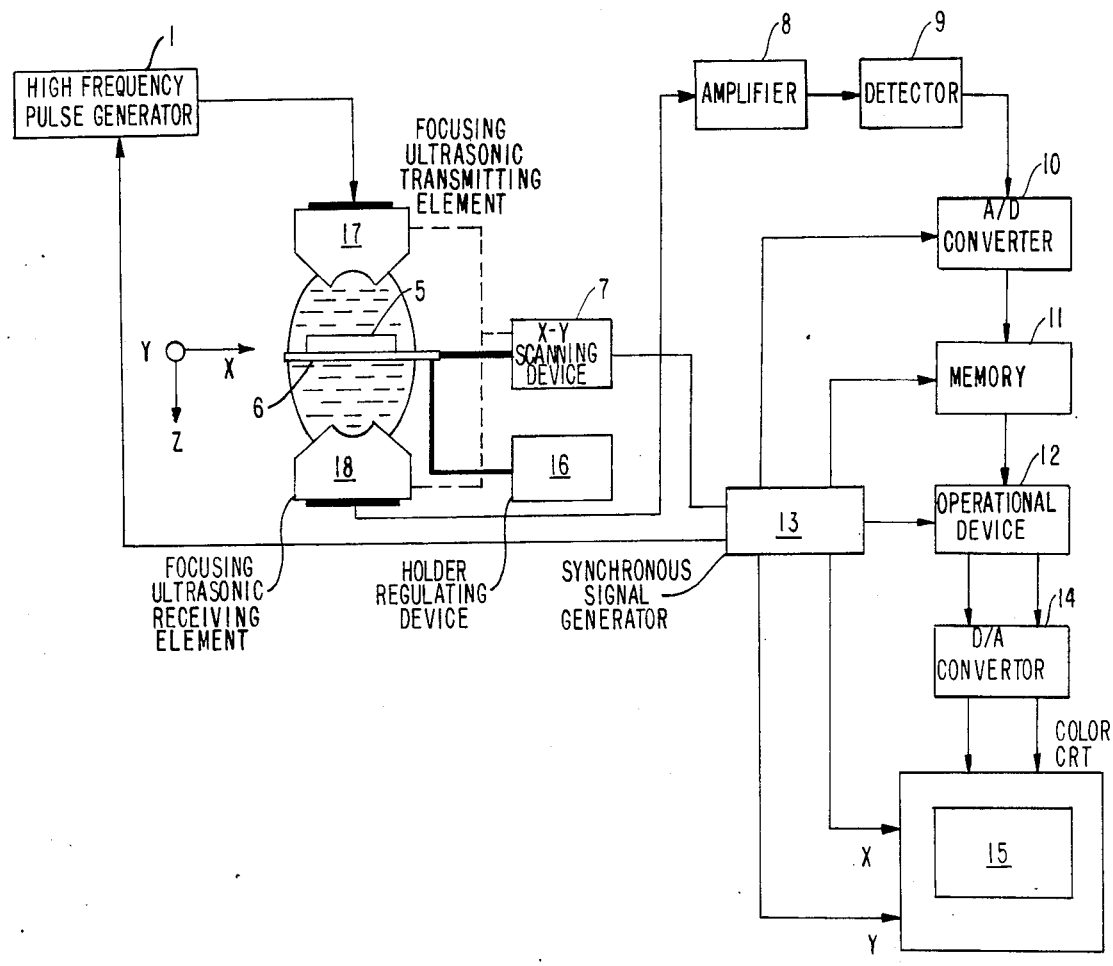
FIG. 2 illustrates a schematic block diagram of another embodiment of the present invention.

Referring to FIG. 2, the output terminal of the high frequency pulse generator 1 is connected to a focusing ultrasonic transmitting element 17 and a focusing ultrasonic receiving element 18 is positioned on the opposite side to the focusing ultrasonic transmitting element 17. The sample 5 mounted on the sample holder 6 is positioned between the focusing ultrasonic transmitting element 17 and the focusing ultrasonic receiving element 18. The amplifier 8 as shown in FIG. 1 is connected to the ultrasonic receiving element 18. The X-Y scanning device 7 moves the sample holder 6 in the X-Y direction, but the focusing ultrasonic transmitting vibrator 17 and the focusing ultrasonic receiving element 18 are moved by the X-Y scanning device 7 instead of the sample holder 6.

By this embodiment, color modulated images can be obtained as explained in the embodiment of FIG. 1.

What is claimed is:

1. A multi-color displaying ultrasonic microscope comprising:
    means for transmitting ultrasonic waves from a focusing ultrasonic transmitting element to an object to be inspected,
    means for detecting with a focusing ultrasonic receiving element the ultrasonic waves reflected and/or passed through the object while providing relative shifting of the focusing ultrasonic transmitting and receiving elements with respect to the object,
    means for providing said relative shifting of the focusing ultrasonic transmitting and receiving elements with respect to the object in an X or Y direction,
    means for producing a first signal from a first detected ultrasonic wave and a second signal from at least one of:
    (a) said first signal;
    (b) a second detected ultrasonic wave shifted in frequency from said first detected ultrasonic wave, and
    (c) said second detected ultrasonic wave focussed to a different depth than said first detected ultrasonic wave, and
    means for displaying the two signals on a color cathode ray tube as a color image modulated by two different colors, respectively.

2. A multi-color displaying ultrasonic microscope according to claim 1, wherein said second signal is a reciprocal of said first signal.

3. A multi-color displaying ultrasonic microscope according to claim 1, wherein said means for producing a first signal and a second signal produces a third signal from said second detected ultrasonic wave, and produces said second signal as a difference signal of said first and third signals.

* * * * *